United States Patent
Jain et al.

(10) Patent No.: US 6,362,219 B1
(45) Date of Patent: Mar. 26, 2002

(54) PROCESS FOR THE PREPARATION OF A FORMULATION OF DIHYDROARTEMISININ FOR THE CONTROL OF WIDE SPECTRUM OF MALARIA

(75) Inventors: Dharam Chand Jain; Rajendra Singh Bhakuni; Ram Prakash Sharma; Sushil Kumar; Guru Prakash Dutta, all of Lucknow (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/704,485

(22) Filed: Nov. 2, 2000

Related U.S. Application Data

(62) Division of application No. 09/264,352, filed on Mar. 5, 1999, now Pat. No. 6,214,864.

(30) Foreign Application Priority Data

Feb. 12, 1999 (IN) .......................... 236/DEL/99

(51) Int. Cl.$^7$ .................. A61K 31/335; A61K 31/20
(52) U.S. Cl. .................. 514/450; 514/560; 514/895
(58) Field of Search ................ 514/450, 560, 514/895

(56) References Cited

U.S. PATENT DOCUMENTS

| | | | |
|---|---|---|---|
| 5,225,427 A | 7/1993 | Venugopalan | 514/378 |
| 5,677,331 A | 10/1997 | Zhou et al. | 514/450 |
| 5,834,505 A | 11/1998 | Peters | 514/454 |
| 5,955,084 A | 9/1999 | Jain et al. | 424/195.1 |
| 6,214,864 B1 * | 4/2001 | Jain et al. | 514/450 |

OTHER PUBLICATIONS

Looareesuwan, S. et al. "A Comparative Clinical Trial of Sequential Treatments of Severe Malaria With Artesunate Suppository Followed . . . Thailand" Am.J.Trop.Med.Hyg. vol. 57, No. 3, p. 348–353, (1997).

Gomez Landires, E.A. "Efficacy of Artesunate Suppository Followed by Oral Mefloquine in the Treatment of Severe . . . Ecuador" Jpn.J.Trop.Med.Hyp. vol. 24, Suppl. 1, p. 17–24, (1996).

Looareesuwan, S. et al. "Artesunate Suppository for Treatment of Severe Falciparum Malaria in Thailand" Jpn-.J.Trop.Med.Hyp. vol. 24, Suppl. 1, p. 13–15, (1996).

Thwe, Y. et al. "Artesunate Suppository—Mefloquine Tablets (Plasmotrim, Rectocaps, Mefloquine, Lactab) in the Treatment . . . Malaria" Jpn.J.Trop.Med.Hyp. vol. 24, Suppl. 1, p. 25–32, (1996).

Bhatt, K.M. et al. "Efficacy and Tolerability of a Sequential Artesunate Suppository–Mefloquine Treatment of Severe . . . Malaria" Jpn.J.Trop.Med.Hyp. vol. 24, Suppl. 1, p. 59–63, (1996).

Kyaw, W. et al. "Efficacy of Artemether and Artesunate Suppositories (Rectocaps) in the Treatment of Uncomplicated Falciparum Malaria" Jpn.J.Trop.Med.Hyp. vol. 24, Suppl. 1, p. 55–58, (1996).

Arnold, K. et al. "A Randomized Comparative Study of Artesmisinine (Qinghaosu) Suppositories and Oral . . . Malaria" Transactions of the Royal Soc. of Trop. Med. and Hyphne vol. 84, p. 499–502, (1990).

* cited by examiner

*Primary Examiner*—Kevin E. Weddington
(74) *Attorney, Agent, or Firm*—Ladas & Parry

(57) ABSTRACT

The present invention relates to a synergistic formulation useful for the control of wide spectrum of malarial infections, which comprises a pharmaceutically effective amount of dihydroartemisinin and a vegetable oil.

6 Claims, No Drawings

PROCESS FOR THE PREPARATION OF A FORMULATION OF DIHYDROARTEMISININ FOR THE CONTROL OF WIDE SPECTRUM OF MALARIA

This appln is a Div. of Ser. No. 09/264,352 filed Mar. 5, 1999, U.S. Pat. No. 6,214,864.

FIELD OF THE INVENTION

This invention relates to the formulation of artemisinin derivative (Dihydroartemisinin) for the emergent treatment and control of uncomplicated/severe complicated/cerebral and multi-drug resistance malaria. Dihydroartemisinin is a lactol derivative of artemisinin (Qinghaosu), the principle antimalarial constituent of the plant *Artemisia annua*.

BACKGROUND OF THE INVENTION

Malaria is caused by blood protozoa of the genus Plasmodium. The four species of Plasmodium that infect humans are *Plasmodium vivax, P. malariae, P. ovale* and *P. falciparum*, the last one is responsible for producing severe complications and cerebral malaria, which can cause the patient to lapse into a coma and ultimately leads to death. In many parts of the world, strains of *P. falciparum* have emerged which are resistant to chloroquine, mefloquine, halofantrinc, quinine and sulfadoxin+pyrimethamine combination, and sulfa methodpyrazine+pyrimethamine combinations the trusted drugs of choice for control of malaria. Like-wise *P. vivax* infections resistant to chloroquine are emerging in different countries. More than 270 million people suffer from the disease, and 1.2–1.7 million deaths occur yearly. Mortality is more among children under 5 years of age who are specially sensitive because of their lack of immunity to the disease (Ziffer H; Highet RJ and Klayman DL; Artemisinin an endoperoxide antimalarial from *A. annua*. Progress in the chemistry of organic natural product: Herz W (Ed.). Springer-Wien New York, 1997. P. 121–214).

Severe complicated malaria is a life-threatening condition and comatose cerebral malaria cases need emergency parental therapy. Severe *P. falciparum* infections are common in both rural and urban areas and the management of these cases becomes difficult because of emerging problems of drug resistant infections. The comatose cases generally do not survive more than 72 hrs and therefore, require urgent antimalarial drug therapy. The suppository preparations of a variety of antimalarials can be effectively used as emergency treatment in rural areas as well as primary health care centres and these can be easily administered even by unskilled health workers in remote areas. Several reports have been published which support the observation that rectal suppository preparations of artemisinin have powerful effect in reducing the falciparum parasitaemia in critically sick and severe cases including cerebral complications (Vinh et al. (1997); Trans Roy Soc. Trop. Med. Hyg. 91, 465–467; Li et al 1985. J Trad. Chinese Med. 5, 159–161).

The endoperoxides are a promising class of antimalarial drugs which may beet the dual challenges posed by drug parasites and the rapid progression of severe malarial illness and complications which can prove fatal unless emergency treatment is instituted. Artemisinin, is a sesquiterpene lactone containing an endoperoxide bridge (—O—O—C) and is unique among the antimalarial drugs. Dihydroartemisinin (DHA) is the reduced lactol derivative of artemisinin and the semisynthetic derivatives (artemether, arteether, artesunate and artelinate) are ethers or esters of the lactol. In general, the endoperoxides present in all these derivatives, have several advantages over existing antimalarial drugs. These derivatives show little or no cross-resistance to existing anitmalarials. The endoperoxides are fast-acting and clear the periphera blood of parasites more rapidly than other available drugs and finally resistance to the endoperoxides has not yet developed, despite widespread clinical trials. (White N.J., 1994, Artemisinin Current Status: Trans R. Soc. Trop Med Hyg. (88 Suppl). 53–54). The attractive feature of the drugs (arteether, artemether) is the lack of systemic neurotoxicity at the clinically prescribed doses (Looaresuwan, S. et al. 1997 Acta. Tropica. 67, 197–205).

Prior art

Dihydroartemisinin (DHA) is the simplest semisynthetic derivative of Artemisinin, the principle antimalarial constituent of medicinal plant *Armeisia annua* (Warburton, D. (1984) Handbook of Experimental Pharmacology, MaCmillan NY pp. 471–495; Hoffman, S. L. (1986). Clin. Trop. Med. Communicable Dis. 1, 171–274). It has considerable activity in vivo and in vitro and is 3.8 to 5 times more potent than artemisinin (de Vries, P. et al (1996). Drugs 52, 818–836; China Cooperative Research group on Qinghaosu, (1982b) J. Trad. Chin. Med. 2, 17–24); Gu, H. M. et al, (1984) Trans. Roy. Soc. Trop. Med. Hyg, 78, 265–270). In vitro bioassay against drug-resistant *P. falciparum* cultures (W-2 Indo-China and D-6 Sierre Lone strains) showed that direct antimalarial activity of DHA is superior to that of artemether and arteether β (Lin, A. J. et al (1987) J. Med. Chem. 30, 2147–2150). However, because of its poor solubility in water, DHA had only been formulated as an oral preparation (Tablet) (Li, Q. G. et al (1998) J. Pharm. Pharmacol. 50, 173–182). DHA has been chiefly used for making semisynthetic derivatives such as artemether (AM) and arteether (AE) which are soluble in oil, and the water soluble drug artesunate (AS) (Luo, X. et al, (1984) Helv. Chem. Acta. 67, 1515–1522; Lin, A. J. et al, (1987) J. Med. Chem. 30, 2147–2150; Brossi, A. et al, (1988) J. Med. Chem. 31, 645–650). Zhao and Song (1993 Yao Hsuch Pao, 28, 342–346) compared the pharmacokinetics of oral dihydroartemisinin (DHA) and qinghaosu (QHS) Tablets in human volunteers and reported very high bioavailability of DHA (oral tablets) as compared to QHS (oral) and serum level after QHS were only 1.6–10.8% that of oral DHA preparation. For oral administration DHA was reported to be far superior blood schizontocide compared to QHS. Qi-Gui Li et al (1998 J. Pharm. Pharmacol. 50, 173–182) compared the oral bioactivity of dihydroartemisinin (DHA) with artemether, arteether and artesunic acid in rats and concluded that maximum plasma concentration was produced by oral DHA (769±218) in comparison to artemether (381±113), arteether (324±10) and artesunic acid (208±25 ng ml$^{-1}$). Further area under plasma concentration time curve (ngh ml$^{-1}$) was highest with oral DHA 9615±56) as compared to artemether (306±52), arteether (298±68) and artesunic acid (217±34). Elimination half life (h) was longer for DHA (4.94±0.73) as compared to artemether (2.04±0.18), arteether (1.79±0.47) and artesunic acid (1.34±26 h). DHA was reported to be active metabolite of other artemisinin derivatives such as artemether (AM), arteether (AE), Artesunate (AS) Artelinic acid (AL).

Benakis et al (1996) administered (60 mg dose representing half of daily dose) oral dihydroartemisinin tablets to six uncomplicated falciparum malaria cases and the peak plasma levels of dihydroartemisinin (0.26–0.71 µg/ml) were recorded between 1 . 2 hrs in four subjects. Thereafter, plasma level dropped and there was complete excretion by 6 hrs. Elimination half-life of DHA was 0.71–1.45 h, drug was well tolerated in 2 subjects while 4 subjects experienced mild headache, nausea or vomiting. One subject showed gastrointestinal hemorrhage and stupor 30 min after drug (Tablet) administration. Benakis et al (1996 J. Trop. Med. Hyg. 24, Suppl 1, 7–11) suggested that the development of a sustained release form of DHA could overcome the adverse drug reaction of table form of drug.

Benakis et al (1977) also reported that following oral artesunate administration, the maximum dihydroartemisinin, plasma level produced was much higher 0.57±0.18 µg/ml compared to that of parent compound artesunate which recorded peak level of 0.12±0.11 µg/ml. It may be emphasized, that DHA level was 5-fold higher compared to that of artesunate and that DHA is the main antimalarial principle following artesunate administration. Further it was pointed out that for artesunate type of antimalarials, dose administration (every 3 hourly) would be necessary because of a very short half-life of the drug. However, Bethell et al (1977 Trans R. Soc. Trop. Med. Hyg. 91, 195–198) had observed wide variation in peak plasma concentration of DHA (664 ng of DHA/ml, 95/Cl 387–9410, range (79–1394) in Vietnamese *P. falciparum* cases who were administered oral artesunate.

The initial studies with artemisinin suppositories were carried out in China for the control of *P. falciparum*. The suppository treatment was found satisfactory as shown by fever clearance time (15–39 h) and parasite clearance time (35–52 h) (Li et al, 1989, IV World Cong. Clin. Pharmacol. & Therapeutics, Munnich-Heidel-berge, Germany, July 1989). Arnold et al (1990; Trans Roy. Soc. Trop. Med. Hyg. 85, 499–502) reported that artemisinin suppositories (Containing 2800 mg total drug administered in 56 h) produced complete parasite clearance in 41.8 h in cases with acute *P. falciparum* infection, while those receiving quinine (Oral) at 1500 mg dose daily×14 days would take 68.1 for parasite clearance.

Hien et al (1991 Trans. Roy. Soc. Trop. Med. Hyg. 84, 499–502) had reported that artemisinin (600–2200 mg) suppositories rapidly cleared asexual *P. Falciparum* parasites in children and confirmed the problem of high incidence recrudescence with this drug. Suppositories could be used as presumptive treatment to prevent the development of high parasitaemia. In the study 10 children receiving 10–mg/kg artemisinin took 18.9±4.7 hrs to achieve initial 95% clearance of parasitaemia.

Astesunate suppositories (1600 mg dose administered over 3 days) were evaluated by Looareesuwan et al (1997, Am J. Trop. Med. Hyg. 57, 348–53) and (200 mg×3 days) by Kyaw et al. 1996. According to these workers, the artesunate suppositoreis achieve complete parasite clearance at a fantastic speed (16–36 h) as good as that achieved by oral tablet of artesunate. Patients with cerebral symptoms and altered conscious levels generally give a good response and recover. Rectal suppositories were able to control severe complications of *P. falcipurum* cases better than im artemether as shown by time to regain full consciousness in comatose cases.

Artemisinin suppository treated cases look 24 (18–30) h for recovery from coma, while artemether took 47 h (31–63 h). The efficacy of rectal artemisinin suppository was equal to iv artesunate which is considered to be most fast-acting treatment for comatose cases as reported by Hein et al. (1992). The development of rectal formulation would provide a better alternative to the oral treatment in terms of quick absorption, high bio-availability and effective plasma level adequate to exert antimalarial effect in the blood.

The fast excretion rate would justify the repeated rectal administration every 4 hrs initially to control severe complicated infections, without causing any toxicity. Rectal suppository are simple to administer, easy to store at room temp and its administration does not require any special equipment, and can be given as emergency drug at rural health centres throughout the developing world where malaria related mortality is high.

The water soluble derivative of DHA, namely the artesunate acid has been found to be very effective against malaria in vitro and has got low toxicity in vivo and in vitro (Yang, Q. et al (1982) J. Trad. Chin. Med., 3, 99–103; Lin, A. J. et al (1987) J. Med. Chem. 30, 2147–2150). Although Artesunate (AS) is 3.2 time more potent than artemisinin and is less toxic than artemether, it has limited stability in solution (Zhou, Z. M. et al (1987) J. Chromato 414, 77–90; Panisko, M. D. and Keystone, J. S. (1990) Drugs, 39, 160–189) and dose must be prepared immediately before administration. Pharmacokinetic data obtained in man, rabbit, rat and dog suggested that artesunic acid is distributed and hydrolysed to DHA by plasma esterase with an elimination half-life of 2–4 min in rabbits and 27 min in dogs (Zhao, K. C. et al (1986) Acta. Pharm. Sin. 21, 736–739). Due to its rapid and extensive conversion to DHA, artesunic acid could be considered a prodrug of DHA (Titulaer, H. A. C. et al, Int. J. Pharm. 69, 83–90,1991). The pharmacodynamic activity of artesunate is due to the metabolite (DHA) rather than to be administered product.

Karbwang, J. et al (1998) (Ann. Trop. Med. and Parasitol, 92, 31–36) studied the pharmacokinectics of artemether (oral) and its conversion to DHA in *P. falciparum* cases and concluded that DHA was believed to be the main determinant of the successful treatment, suggesting that anitmalarial activity corresponded to DHA level in plasma. Plasma level of DHA metabolite was nearly three fold higher in patients with sensitive *P. falicparum* infection. The mean ratio of inhibitory activities of artemether vs. DHA against *P. falciparum* isolates in Thailand was 1:2.9 within 6–12 hrs, the plasma artemether levels decreased fast, while DHA level was still higher. However, both artmether and artesunate are susceptible to breakdown by humidity, light and acidic conditions at room temperature. An aqueous solution of sodium artesunate at pH 7–8 hydrolyses within 1 h to DHA.

DHA is a major metabolite of artemether, arteether and artesunic acid/artesunate in vivo (de Vriens, P. J. and Dien, T. K. (1996) Drugs, 52, 181–836; Chi, H. T. et al (1991) Biol Mass Spectrum 20, 609–628; Zhou, Z. M. et al (1987) J. Chromatog, 414, 77–90; Li, Q. G. (1998) J. Pharm. Pharmacol. 50, 173–182). The high rate of malaria recrudescence associated with other artemisinin derivatives has been ascribed at least partly to short plasma half-life.

The pharmacodynamic activity of artemether in healthy adults was reported to be due to the metabolite DHA rather than administered prodrug. The main metabolite DHA is approximately three times as active as the parent compound in terms of antimalarial activity against *P. falicparum* (Teja-Isavadharm, P. et al (1996) Br. J. Clin. Pharmacol. 42, 599–604). The contribution of other unidentified metabolites to antimalarial activity was reported to be negligible ((Lee, I. S. and Heefford, C. D. (1990) Pharmacol Ther.48, 345).

In vivo conversion of arteether (AE), artemether (AM) and artesunate (AS) to DHA in rats was compared via all the three routes (oral, im and rectal) of administration, and the conversion rate was faster with AS followed by AE and AM. The high conversion of AS to DHA can be explained by the fact that AS and DHA show same in vitro antimalarial potency against chloroquine sensitive and chloroquine resistant strains of *P. bergei*. Although the DHA level obtained after dosing with AM, AE and AS were less than 2.6% those after im dosing with DHA, the high antimalarial activity of DHA probably contributes significantly to overall antimalarial activity of these drugs in vivo (Li, Q. G. et al (1998) J. Pharm. Pharmacol, 50,173–182).

The bio-availablility of artemether in healthy subjects given drugs by intramuscular and intra-rectal routes showed that plasma profile of its active metabolite dihydroartemisinin following intarcctal (ir) administration suggested that this route should be assessed as an alternative to intramuscular route in the rural tropics (Teja Isavadharm et al. 1996. Br. J. Clin. Pharmacol. 42, 599–604). The conversion of artesunate to its active metabolite dihydroartemisinin appears unique in antimalarial pharmacology because of its rapid clearance rate. (Benthell et al. b1998, Br. J. Clin Pharmacol. 45, 123–129).

The im bio-availability of AM and AE were very low, indicating incomplete absorption of these drugs atleast during first 8 h after im administration. The bio-availability of DHA on the other hand, is midway between other oil soluble drugs and water soluble drugs. The relatively slow and incomplete bio-availablity of both 1M and oral preparation of artemether is of some concern as this is a front line treatment for severe and complicated falciparum malaria. The im absorption of artemether in children with severe malaria (Cerebral malaria (CM) accompanied with respiratory distress was reported to be erratic and five CM cases did not show plasma DHA levels in one study (Murphy, S. A. et al.(1997) Trans. Roy. Soc. Trop. Med. Hyg. 91, 332–334). In view of the impaired absorption of artemether in children, there is an urgent need to develop an effective antimalaria for children. Oral artemether has been reported to undergo inadequate drug absorption in *P. falciparum* cases which resulted in recrudescence (Bangchang, K. N. A. et al (1994) J. Chem. Pharmac. 37, 249–253). Clinical investigators therefore, advocate the replacement of artemether with iv artesunate preparation for treatment of severe malaria in children (Murphy, S. A. et al (1997) Trans. Roy Soc. Trop.Med. Hyg. 91, 332–334).

The plasma level of DHA by im route were sustained over 30 hr and parasitidal effect was maintained for much longer time period compared to oral or Intarectal route (DHA activity by im route, AUC 3445 n Mlo $l^{-1}$ h compared to oral route 3855 n mol$^{-1}$ h but activity due to DHA was prolonged beyond 30 h while the oral dose provided effective level upto 10 h (Teja-Isavadharm, P. et al (1996) Br. J. Clin. Pharmacol. 42, 599–604).

The earlier work on artemisinin, arteether, artelinate, artesunate administered by im formulations and arteether and DHA administered by oral route have shown good gemetocidal activity both in animal model and against *P. falciparum*. These drugs have potential for the interruption malaria transmission. (Dutta, G. P. et al (1989) Chemotherapy (Bansal) 35, 2000–2007; Tripathi, R. et al (1990), Amer. J. Trop. Med. Hyg. 43, 571–575; ibid, (1985) 54, 652–654).

Cost is a critical factor in determining use of antimalarial drugs. Artemisiinin derived drugs are now available commercially in a few countries but they are restricted because of high cost, eg., oral artesunate currently cost about $5–6 per treatment as compared to $1.85 for mefloquine and 7° C. for drugs such as chloroquine. Injectable artesunate, artemether and arteether cost even more compared to quinine injections at less than $2.0 per treatment.

There is undoubtedly a real need for an effective new antimalarial drug based on artemisinin or its semi-synthetic derivatives with improved absorption, bio-availability, high plasma drug concentration for longer duration of time and cost effectivenss for the treatment of multi-drug resistant and severe complicated/cerebral malaria.

The main object of the present invention is to develop a formulation of dihydroartemisinin for the control of wide spectrum of malaria.

Anotehr object of invention is to develop improved safe formulation, less expensive, for uncomplicated malaria infections as well as for the control of multi-drug resistant malaria and emergent treatment of severe complicated cerebral malarial infections.

Still another object of invention is to develop a formulation which will be able to stop malaria related mortality among children and adults.

SUMMARY OF THE INVENTION

The present invention is to develop an improved formulation of artemisinin derivative for the control of both uncomplicated malaria and for the emergent treatment of severe complicated and cerebral malaria cases and for the treatment of multi-drug resistant malarias. This formulation comprises preparation of artemisinin derivative in sterile, neutralized refined oil which would exert fast acting blood schizontocidal activites in adults and children and has long shelf-life. The antimalarial profile of the formulation given by different routes (rectal, intramuscular and oral) has confirmed high activity.

DETAILED DESCRIPTION OF INVENTION

For the present invention we have chosen to develop a formulation of dihydroartemisinin for the following reasons: The product is superior to the original molecule, artemisinin in terms of efficacy. Dihydroartemisinin is simplest one step, high yield and economic semi-synthetic derivative of artemisinin. Dihydroartemisinin is known to be an active metabolite of artemether, arteether, artesunic acid, and artelinic acid which is responsible for the antimalarial activity of these drugs (Lee, Q. G. et al (91998) J. Pharm. Pharmacol. 50, 173–182).

The antimalarial profile of the compound given by oral route has been confirmed by high activity of dihydroartemisinin formulation. The oral route of administration is important for treatment in villages as well as in rural and urban areas. The oral formulation gives 100% cure rate against MDR *P. yoelii nigeriensis* malaria and the efficiency is better than QHS (artimisinin) and its other derivatives used by earlier workers which are effective upto 50–90% at exceptionally high doses. Comparable antimalarial effects can be achieved with DHA at safe and low dose whereas high doses of QHS upto 5.0 g dose gives cure rate 55%, Artemether upto 700 mg give cure rate 90% and artesunate upto 750 mg gives cure rate 70–90%. Safety of DHA formulaation is better than artemether and artesunate.

The route of administration is important for the emergency treatment of severe complicated/cerebral malaria (Shen et al 1989, Antimalarial drug development in China 31–45; Hein, T & White NJ (1993) Lancet 34, 603–608). The DHA rectal formulation is simple to administer, easy to store and its administration does not require any special equipment. In order to achieve higher efficacy, the repeated rectal administration of the drug every 4–6 hrs initially, to control severe complicated infections without caussing any toxicity.

An intramuscular DHA formulation would be effective in controlling severe complicated *P. falciparum* infections. The im formulation would not need an intravenous infusion apparatus. Intramuscular DHA is ready to use, unlike intravenous artesunate which is available in the form of an ampoule of lophilizate and an ampoule of solvent which must be mixed before use. The prepared solution of artesunate is not very stable on storage and injection must be given rapidly, Moreover, the risk of accidental overdose is certianly less in im than with an iv prepartion.

According to Li et al (1988, J. Pharm. Pharmacol. 50, 173–182), the maximum plasma concentration by im route attained in rats with DHA is very high in comparision to arteether as well as artemether (DHA 1579±443; AM 692±234 and AE 160±12.4). From the Pharmacokinetic point of view the half-life of DHA is longer than that of other artemisinin derivatives (DHA 4.44±0.27 h vs AE 362±0.9 h vs AM 1.78±0.80 h). When the cytotoxicity of artemisinin and dihydroartemisinin were compared with ethers and esters of dihydroartemisinin, it could be seen that dihydroartemisinin was significantly less cytotoxic than artemether, arteether, artelinic acid and sodium artelinate (Woerdenbag et al. J. Nat. Prod. 56, 848–56, (1993). The absorption (%) of DHA within 8 h is 85.4±12.1 which is much higher than AM (54.2±25.9) and AE (34.0±9.6).

Comparison of Main Pharmacokinetic parameters of DHA, AM, AE and AS in rates after single IM dose

| Parameter | DHA Dihydroartemisinin | AM Artemether | AE Arteether | AS Artesunate |
|---|---|---|---|---|
| 1) Maximum plasma Concentration (ng ML$^{-1}$) | 1579 ± 443 | 692 ± 234 | 160.7 ± 12.4 | 1650 ± 446 |
| 2) Time of maximum plasma Concentration (min) | 17.5 ± 2.89 | 28.8 ± 11.8 | 41.4 ± 14.7 | 15.0 ± 4.1 |
| 3) Area under plasma concentration (h ml$^{-1}$) | 2719 ± 38.5 | 1007 ± 48.1 | 285.7 ± 80.5 | 773 ± 398 |
| 4) Distribution half life (h) | 0.73 ± 0.13 | 0.23 ± 0.04 | 0.34 ± 0.07 | 0.15 ± 0.06 |
| 5) Elimination half life (h) | 4.44 ± 0.27 | 1.78 ± 0.80 | 3.62 ± 0.09 | 0.54 ± 0.14 |
| 6) Mean absorption time (h) | 0.21 ± 0.04 | 0.14 ± 0.04 | 0.25 ± 0.06 | 0.11 ± 0.07 |
| 7) Absorption 0–8 h (%) | 85.4 ± 12.1 | 54.3 ± 25.9 | 34.0 ± 9.6 | 104.7 ± |

In contrast to above artemisinin derivatives dihydroartemisinin (DHA) seems to be a good antimalarial candidate as it has the highest plasma concentration, the highest binding capacity in RBC, the longest elimination half life and the lowest toxicity. The absorption of DHA in 8 h is very high in comparison to other drugs. DHA is a major metabolite of all these drugs and antimalarial activity of these drugs is due to major metabolites DHA. DHA showed the low rate of recrudescence in comparision of artemether and arteether. Therefore, the dihydroartemisinin has been synthesized and stable sormulation with enhance bio-availability was prepared for the control and emergent treatment of uncomplicated/severe complicated/cerebral malaria and multi-drug resistant malaria infections.

Accordingly, the present inventoin provides a formulation of the dihydroartemisinin for the control of wide spectrum of malaria which comprises (a) preparation of dihydroartemisinin from artemisinin by known method, (b) dissolving dihydroartemisisin in sterilzed neutral refined vegetable oil by heating at 70–90° C. for 2–4 min and cooling the solution at room temperature to obtain the desired formulation.

The invention further provides a formulation which shows no adverse gastric effects, hemorrhage etc. which are found in the treatment with dihydroartemisinin tablet.

The invention further provides a formulation which provides maximum bio-availability in comparison to other artemisinin derivatives, selected from artemether and arteether.

The invention further provides a formulation which has more than 80% absorption of compound within 8 h, which is much higher than other artemisinin derivatives (artemether, arteether).

In another embodiment of the invention, wherein dihydroartemisinin and the vegetable oil is present in a ratio of 0.22–0.33:1 w/w.

In another embodimetn of the invention, the refined vegetable oil used for prepartion, is selected from groundnut oil, sesame oil, tea oil etc.

In another embodiment of the invention, the dihydroartemisinin used in the preparation appears in mixture of α and β tautomers with the ratio of and β in the solvent chloroform (1:1) and methanol (2:1).

In another embodiment of the invention, the dihydroaretmisinin used in the formulation has the following characteristics: MP:(153–154° C.), MW: 284, MF: $C_{15}H_{24}O_5$.

The invention provides a formulation which is viscous in nature and light yellow in colour.

The invention further provides a formulation which is safe, well tolerated and better than artemether and artesunate of its safety.

The invention further provides a formulation which has shelf life of atleast two years;

The invention further provides a formulation which as 200–300 times more accumlation in the malarial infected red blood cells than the normal red blood cells showing the high antimalarial potential of this formulation.

The invention further provides a formulation which is fast acting, having blood schizontocidal activity and useful for the treatment of uncomplicated/severe complicated/cerebral and multi-drug resistant malarial infections.

The invention further provides a formulation which is effective against multi-drug resistant *Plasmodium yoelii nigerienses* parasite which is resistant to high oral dose of chloroquine, amidoquine, mapaerine, mefloquine, quinine and halofantrine.

The invention further provides a formulation which is the safe subsitute of Primaquine and useful for interrupting transmission of *P. falciparum* and other malarial infections.

The invention further provides a formulation w hich can be administered through oral, intrarectal and intramuscular routes and reduce the gamatocidal effect.

The invention provides a formulation from which has no adverse mat hemoglobin type of toxicity which is known to be assocated with administration of primaquine.

The invention further provides a formulation which is effective against blood asexual stage as well as sexual stage of the both *P. falciparum* and *P. vivex* parasites.

The invention futher provides a formulation which can be used through oral route for control of uncomplicated *Plasmodium falciparum* and *P. vivex* infections.

The invention further provides a formulation which can be used through oral route for control of chloroquine resistant and halofantrine resistant *P. vives* malaria.

The invention further provides a formulation which can be used through oral route for control of multi-drug resistant *P. falciparum* infections caused by chloroquine, mefloquine, quinine, amidoquine and halofentrine.

The invention further provides a formulation which can be used through oral route for control of treatment of *P. malariae* and *P. ovale* infections.

The invention further provides a method of treatment of malaria through oral route by administration of a daily dose in the three divided doses (every 8 hrs) to reduce the recrudescence rate of malaria.

The invention futher provides a formulation which can be used through intrarectal route for emergent treatment and control of uncomplicated, severe complicated/cerebral and multi-drug resistant malarial infections.

The invention further provides a formulation which can be used thorugh intrarectal route for rectal suppository for the fast action.

The invention further provides a formulation which can be used through intrarectal route for the emergent treatment of severe, complicated and comatose cerebral malaria infection to prevent progression of the disease.

The invention further provides a formulation which can be used through intrarectal route for the treatment of children in severe complicated malaria and prevent mortality and the progression of severity of these disease.

The invention further provides a formulation which can be used through intrarectal route for as emergent and life saving treatment of severe comatose and cerebral malaria cases.

The invention further provides a method of treatment of malaria which can be used through intrarectal route by administration of the formulation daily in two or three divided doses at 8–12 h interval to control the malarial infection.

The invention further provides a formulation which can be used through intramuscular route for emergency life saving treatment for severe complicated and cerebral malaria.

The invention further provides a formulation which can be used through intramuscular route for the fast recovery of the comatose patients.

The invention futher provides a formulation which can be used through intramuscular route for the complete cure of the uncomplicated, severe complicated/cerebral malaria and multi-drug resistant malaria infections.

The invention further provides a formulation which can be used through intramuscular route to prevent and interrupt malarial transmisson to stop multi-drug resistance in the patients.

The invention further provides a method of treatment of malaria through intramascular route by administration of the formulation by daily injection in two divided doses for five consecutive days for adults. Doses will be correspondingly reduced for children and infants.

This invention is described in detail in the following example. However, it should not be construed to limit the scope of the present inveniton.

EXAMPLE

Chemistry, formulation and Antimalarial evaluation of dihydroartemisinin (DHA):

a) Preparation of dihydroartemisinin from artemisninin:

Artemisinin (10 g) in 250 ml of methanol, was cooled in an ice bath to 0° C. To the stirred solution was added 4 g of $NaBH_4$ over a period of 30 min. The reaction mixture was stirred for 1 h after complete addition of $NaBH_4$. The crushed ice was added to the reaction mixture which produced a precipitate immediately. The white precipitate was filtered and washed with cold water. The precipitate was dissolved in $CH_2Cl_2$ (250 ml) and dried over anhydrous sodium sulphate. The solvent was evaporated under vacuum and residue was recrystallized with ethylaceteate-hexane (1:3) solvent which yielded (9.1 gm) of pure crystalline substance of mp 151–153° C. The dihydroartemisinin MF: $C_{15}H_{24}O_5$; MW 284) has been found to be a hemiacetal and exist as a mixture of a α and β anomers whose ratio is solvent dependent. When dihydroartemisinin is crystalline, the hydroxyl at β-position but when in solution, a mixture of epimers is formed. The ratio of α and β isomers in the $^{13}CNMR$ of dihydroartemisinin was found to be (1:1) in $CDCl_3$ and (2:1) in $CD_3OD$ solvent. (Pathak et al. Ind. J. Chem. 34B, 992–93 (1995). The material was characterized by spectral methods (IR, $^1H$ NMR, $^{13}C$ NMR & mass) and authentic sample.

b) Formulation of dihydroartemisinin (DHA):

Dihydroartemisinin (DHA) 200 mg was taken in sterile refined neutralized (10 ml) groundnut oil and dissolving by mild heating at 80–90° C. and cooling the solution at room temperature. The formulation was stored at room temperature till use. It has been found to be stable at room temperature for several months.

(c) Antimalarial efficacy:

Test Parasite: Multi-drug resistant *Plasmodium yoeli nigerienes* (Rodent malaria strian). The *P. yoeli nigerienses* is a multi-drug resistant strain which is resistant to high oral doses of chloroquine (128 mg/kg×4), amodiaquine (128 mg/kg×4), meperaine (128 mg/kg×4), mefloquine (128 mg/kg×4), quinine (400 mg/kg×4) and halofantrine (32 mg/kg×4). This parasite produces 100% mortality in 20–15 g Swiss mice and it is highly virulent for mice. It is ideal parasite for antimalarial evaluation as it produces acute infection with a spectrum of wide range of multi-drug resistance similar to the spectrum of resistance reported in the field isolates of *P. falciparum*.

(i) Antimalarial (blood Schizontocidal) activity of dihydro-artemisinin formulation by rectal route:

DHA formulation was evaluated in vivo in Swiss mice (20 g). The mice were infected intraperitoneally with parasite (multi-resistant strain of *P. yoelii nigeriensis*) and the infected mice were treated for 5–7 consecutive days (Day 0 onwards) with each mouse does (0.2–0.3 ml oil by rectal route) of a DHA formulation prepared in neutralized ground nut oil. For higher doses (15 and 20 mg/kg) the drug was given in divided doses by rectal route. The tail blood smears of the mice were examined periodically after Giemsa staining upto 30 days post-infections. DHA formulation given by rectal route has shown curative effect against multi-drug resistant rodent infection and severe/virulent/ethal malaria infection as shown by complete absence of parasitaemia till 30 of observation (Table 1).

TABLE 1

Blood schizontocidal activity of dihydroartemisinin against
multi-drug resistant *P. yoalii nigeriensis* infection in Swiss mice
(20 ± 1 g) by rectal route.

| Treatment | Dose mg/kg × days | Parasitaemia % Day 5 | Day 7 | Cure-rate Day 30 (%) |
|---|---|---|---|---|
| DHA (in oil) (Rectal route) | 5 mg/kg × 7 | 0.83 ± 1.31 (8) 4-ve | 1.12 ± 1.55 (8) 4-ve | 25 |
| Doses: 5–20 mg | 20 mg/kg × 7 | 0.0 (8) | 0.0 (8) | 87 |
| Control | — | 6 ± 2.92 (8) | 68.87 ± 14.57 (8) | |

Note= No. of mice are given in parenthesis.

Drug is dissolved in sterile ground nut oil for adminisitration.

(ii) Antimalarial (Blood Schizontocidal) activity of dihydro-artemisinin formulation by intramuscular route:

DHA formulation was evaluated in vivo in Swiss mice (20±1 g) as well as baby mice (12±1 g). The mice were infected intraperitoneally with parasite (multi-resistant strain of *P. yoelii nigeriensis*) and the infected mice were treated intra-muscrularly for 5 consecutive days (Day 0,+1,+2,+3,+4) with each mouse dose (0.2 ml oil injection) of a DHA formulation. The tail blood smears of the mice were examined periodically after Giemsa staining upto 30 days post-infection. DHA formulation has shown curative effect against multi-drug resistant rodent infection as shown by complete absence of parasitaemia till 30 days of observation (Table 2).

The DHA formulation given by im route is able to completely control multi-drug resistant *P. yoelii nigeriensis* malaria which is highly fata for Swiss mice. The drug DHA is also effective in controlling severe/virulent/lethal malaria infection in 20–15 g adult mice as well as in baby mice (912±1 g).

TABLE 2

Blood schizontocidal activity of dihydroartemisinin, against
multi-drug resistant strain of *P. yoeli nigeriencsis* in Swiss mice
(20 ± 1 g) and in baby mice 12 ± 1 g by intramuscular route

| Treatment | Host | Dose (mg/kg × days) | Cure rate (%) |
|---|---|---|---|
| Expt. I | | | |
| DHA (IM in oil) Dose 5–30 mg/kg | (20 ± 1 g) | 5 mg/kg × 5 | 100% (8/8) |
| Expt. II | | | |
| DHA (im in oil) Dose 5–10 mg/kg | (20 ± 1 g) | 5 mg/kg × 5 | 100% (8/8) |
| | | 10 mg/kg × 5 | 100% (8/8) |
| Expt. III | | | |
| DHA(im in oil) Dose 5 mg/kg | (12 ± 1 g baby mice) | 5 mg/kg × 5 | 100% (9/9) |
| Control | (20 ± 1 g) | Vehicle (oil) | Nil (0/20) |
| Safety in Healthy mice | 20 ± 1 g mice | 30 mg/kg DHA × 5 | Safe 8/8 |

Drug treatment was started on day 0 (ie day of infection). Mice showing negative blood slide upto day 30 were considered as cured.

(iii) Antimalarial (blood schizontocidal) activity of dihydroartemisinin formulation by oral route:

DHA formulation was evaluated in vivo in Swiss mice (20–25 g). The mice were infected intraperitoneally with parasite (multi-drug resistant strain of *P. yoelii nigeriensis* and the infected mice were treated for 5 consecutive days (day 0 onwards) with each mouse dose of 0.25 ml (in oil) by oral feeding. The DHA formulation is prepared in neutralized sterile ground nut oil. The tail blood smears of treated mice were examined periodically after Giemsa for recording % parasitaemia. DHA formulation given by oral route has shown curative effective against multi-resistant plasmodium which is resistant to high doses of chloroquine, melfoquine, quinine, amodiaquine, mepacrine and halofantrine etc. The DHA oral formulation at 30 mg/kg dose×5 days has shown curative efficacy of 100% against MDR strain of *P. yoelii nigeriensis* (Table 3).

TABLE 3

Blood schizontocidal activity of dihydroartemisinin against
multi-drug resistant *P. yoalii nigeriensis* infection in Swiss mice
(20–25 ± 1 g) by oral route.

| Treatment route | Dose mg/kg × days | Wt. of mice | Parasitamia (%) (Mean ± SD) Days 6 | 7 | 9 | Cure rate (%) 30 |
|---|---|---|---|---|---|---|
| DHA (oral in oil) Control | 30 mg/kg × 5 | 25 ± 1 g | — | — (12) | — (12) | 100 (12) |
| 1 | Vehicle oil | 20 ± 1 g | — | 68.87 ± 14.57 (8) | 75 (1) | Nil |
| 2 | Vehicle oil | 25 ± 1 g | 10.12 ± 3.09 (8) | — | 87.5 ± 3.53 (2) | Nil |

No. of mice are given in parenthesis.

The improved formulation of dihydroartemisinin-the subject matter of this patent offers a number of advantages.

1. The product dihydroartemisinin as oil formulation will be a fast acting, blood schizontocide which would be able to control uncomplicated/severe complicated/cerebral and multi-drug resistant malaria infections.

2. The formulation given by im and rectal route can be used in rural areas where facilities such as constant drip generally used for iv administration of comparable molecule iv artesunate are not available.

3. The rectal administration can be repeated given through syringe or catheter by the family member in village or by paramedical personals as presumptive treatment to control the severity of malaria infections and as emergency treatment to comatose malaria cases and prevent deaths from cerebral involvement in complicated cases.

4. The administration of the formulation by different routes will increase the plasma drug concentration for effective antimalarial treatment. Because of the high efficacy of the formulation IM administration can be given to control the complicated cases cerebral/severe/multi-drug resistant cases.

5. The DHA formulation given by rectal followed by IM route or oral, will exert higher level of antimalarial activity.

6. *P. vivex* sensitive as well as resistant to chloroquine and *P. malariae/P. ovale* infections, can be also controlled by using this formulation and blood stage parasitaemias effectively controlled in uncomplicated cases by oral formulation because of its high efficacy against MDR infection.

7. The oil based oral formulation of DHA would not produce any gastric adverse reactions as reported for DHA Tablets.

8. This formulation will be economically cheaper than the comparable parental preparations like artemether, and artesunate (iv).

9. Safety of this compound on the basis of $LD_{50}$ is comparable to arteether and better than artemether, and artesunate.

10. The formulation is stable at room temperature for longer period.

11. The DHA formulations will be able to prevent deaths of both children and adults due to malaria complications and stop the progression of comatose condition because of their higher antimalarial efficacy, bio-availability and plasma conc.

What is claimed is:

1. A process for the preparation of a formulation useful for the control of wide spectrum of malaria comprising (a) preparation of dihydroartemisinin from artemisinin by known method, (b) dissolving dihydroartemisinin in sterilized neutral refined vegetable oil by heating at 70–90° C. for 2–4 min. and (c) cooling the solution at room temperature to obtain the desired formulation.

2. A process for the preparation of a formulation as claimed in claim 1, wherein the vegetable oil used is selected from groundnut oil, sesame oil and tea oil.

3. A process as claim in claim 1, wherein the dihydroartemisinin used comprises a mixture of α and β tautomers in a solvent.

4. A process as claimed in claim 1, wherein the ratio of α and β tautomers of dihydroartemisinin to the solvent may be 1:1 or 2:1.

5. A process as claimed in claim 1, wherein the solvent used may be selected from chloroform and methanol.

6. A process as claimed in claim 1, wherein dihydroartemisinin and the vegetable oil is present in a ratio between 0.022–0.033:1 w/w.

* * * * *